United States Patent
Kondo et al.

(10) Patent No.: US 7,335,291 B2
(45) Date of Patent: *Feb. 26, 2008

(54) WATER TREATING METHOD, WATER TREATING APPARATUS, AND HYDROPONICS SYSTEM USING THE APPARATUS

(75) Inventors: Yasuhito Kondo, Gunma (JP); Yasuhiko Shimizu, Gunma (JP); Masahiro Iseki, Gunma (JP)

(73) Assignee: Sanyo Electric Co., Ltd., Moriguchi-Shi (JP)

( * ) Notice: Subject to any disclaimer, the term of this patent is extended or adjusted under 35 U.S.C. 154(b) by 701 days.

This patent is subject to a terminal disclaimer.

(21) Appl. No.: 10/275,981

(22) PCT Filed: Apr. 4, 2002

(86) PCT No.: PCT/JP02/03368

§ 371 (c)(1),
(2), (4) Date: May 8, 2003

(87) PCT Pub. No.: WO02/083571

PCT Pub. Date: Oct. 24, 2002

(65) Prior Publication Data

US 2003/0178373 A1    Sep. 25, 2003

(51) Int. Cl.
*C02F 1/461* (2006.01)
(52) U.S. Cl. ............... 205/701; 205/742; 205/758; 204/230.2; 204/262; 204/269; 204/275.1
(58) Field of Classification Search ............ 204/230.2, 204/262, 269, 275.1; 205/701, 742, 758
See application file for complete search history.

(56) References Cited

U.S. PATENT DOCUMENTS 4,062,754 A   12/1977  Eibl ................... 204/268

5,314,589 A *  5/1994  Hawley ................ 205/618
5,770,037 A    6/1998  Goto et al. ............ 205/701

(Continued)

FOREIGN PATENT DOCUMENTS

EP        0 001 285       4/1979

(Continued)

*Primary Examiner*—Arun S. Phasge
(74) *Attorney, Agent, or Firm*—Kratz, Quintos & Hanson, LLP

(57) ABSTRACT

There are provided a water treating method and water treating apparatus which can significantly improve an effect of eliminating microorganisms contained in water intended for drinking and cooking or waster water and a hydroponics system using the apparatus. The method comprises a first treating step of immersing an electrode and carbon fibers capable of collecting at least microorganisms in a passage of for-treatment water and applying a positive potential to the carbon fibers and a negative potential to the electrode so as to adsorb the microorganisms on the carbon fibers, a second treating step of stopping flow of the for-treatment water after completion of the first treating step and increasing the potentials applied to the carbon fibers and the electrode in the presence of the for-treatment water, while polarities of the potentials applied to the carbon fibers and the electrode are kept, so as to cause electrolysis of the for-treatment water, and a third treating step of applying an alternating voltage between the electrode and the carbon fibers in the presence of the for-treatment water after completion of the second treating step.

22 Claims, 4 Drawing Sheets

U.S. PATENT DOCUMENTS 6,814,853 B2 * 11/2004 Kondo et al. ............... 205/701

FOREIGN PATENT DOCUMENTS

| | | |
|---|---|---|
| EP | 1 024 116 A2 | 8/2000 |
| JP | 4-4822 | 1/1992 |
| JP | 9-234459 | 9/1997 |
| JP | 10-180259 | 7/1998 |
| JP | 2002-79251 | 3/2002 |
| WO | 02/00554 A1 | 1/2002 |

* cited by examiner

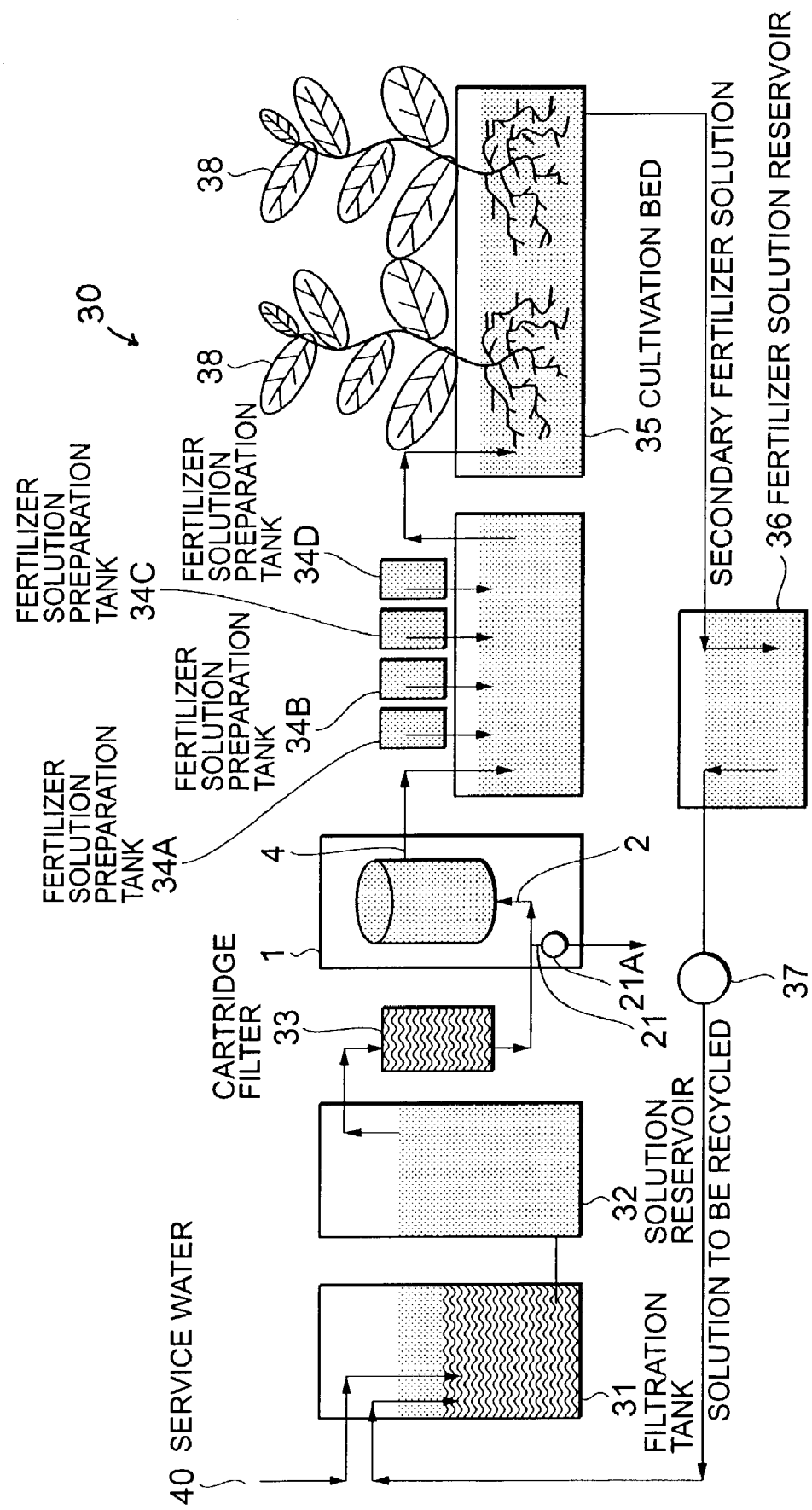

WATER TREATING METHOD, WATER TREATING APPARATUS, AND HYDROPONICS SYSTEM USING THE APPARATUS

BACKGROUND OF THE INVENTION

1. Field of the Invention

The present invention relates to a method and appratus for sterilizing water (water to be treated) (hereinafter, "water to be treated" will be referred to as "for-treatment water") such as water used for drinking and cooking or waste water discharged from hydroponics or a fish hatchery and to a hydroponics system using the apparatus.

2. Description of the Related Art

Heretofore, for example, to remove microorganisms such as bacteria, fungi and protozoans contained in water intended for drinking and cooking such as tap water reserved in a reservoir, a method has been employed in which a porous filter material capable of collecting these microorganisms is placed in a water channel so as to make the microorganisms stick to the filter material and thereby purify the water.

Further, in addition to this, there is also a method in which chlorine and ozone are produced in accordance with electrolysis caused by electrodes immersed in water intended for drinking and cooking and microorganisms contained in the water are eliminated by sterilizing effects of produced chlorine and ozone.

Meanwhile, in hydroponics, a solution prepared by dissolving a fertilizer in water in an amount suitable for cultivation of crops is circulated through a cultivation bed so as to suitably grow crops planted in the cultivation bed. However, the inside of the cultivation bed through which the fertilizer solution is circulated is an environment suitable for proliferation of pathogenic bacteria such as Fusarium (a type of fungi), and if the Fusariums are proliferated in the cultivation bed, they damage roots of the crops and cause the crops to die. Under the circumstances, it has been practiced that the fertilizer solution is heated by means of a heater and that an apparatus which is installed in a translucent jacket and has a structure that pathogenic bacteria contained in the fertilizer solution are killed by ultraviolet radiation or ozone is disposed in a path through which the fertilizer solution is circulated.

Meanwhile, such a filter material collects microorganisms by catching them in fine pores formed on its surface. Therefore, it cannot collect the microorganisms unless they collide against or pass near the surface of the filter material. Consequently, its effect of collecting the microorganisms is limited.

Further, since the microorganisms stick to the filter-material as described above, the filter material eventually becomes saturated and releases the microorganisms in the water channel. Under the circumstances, it is conceivable to heat the filter material so as to kill the stuck microorganisms. However, some microorganisms are resistant to heat, and to ensure a sterilizing effect, the filter material must be heated to a relatively high temperature.

In addition, although the fertilizer solution in the hydroponics is heated so as to kill the pathogenic bacteria proliferated in the cultivation bed, the plants die when the heated fertilizer solution is used as it is. Thus, a cooling device for cooling the heated fertilizer solution is also required. For this reason, there is a problem that a large amount of energy must be consumed so as to heat and cool the fertilizer solution. Further, there is another problem that when the pathogenic bacteria contained in the fertilizer solution are killed by use of ultraviolet radiation or ozone, concentrations of iron and manganese contained in the fertilizer solution are reduced.

The present invention has been conceived to solve the above technical problems of the prior art. An object of the present invention is to provide a water treating method and water treating apparatus which can significantly improve an effect of eliminating microorganisms contained in water intended for drinking and cooking or waster water and a hydroponics system using the apparatus.

SUMMARY OF THE INVENTION

A water treating method of the present invention comprises a first treating step of immersing an electrode and a conductive material capable of collecting at least microorganisms in a passage of for-treatment water and applying a positive potential to the conductive material and a negative potential to the electrode so as to adsorb the microorganisms on the conductive material, a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of applying an alternating voltage between the electrode and the conductive material in the presence of the for-treatment water after completion of the second treating step.

Further, a water treating method of the present invention comprises a first treating step of immersing an electrode and a conductive material capable of collecting at least microorganisms in a passage of for-treatment water and applying a positive potential to the conductive material and a negative potential to the electrode so as to adsorb the microorganisms on the conductive material, a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and a third treating step of applying an alternating voltage between the electrode and the conductive material in the presence of the for-treatment water after completion of the second treating step.

Further, in the forgoing water treating methods of the present invention, the for-treatment water is heated by means of a heater in the third treating step.

Further, a water treating apparatus of the present invention comprises an electrode to be immersed in a passage of for-treatment water, a conductive material which is capable of collecting at least microorganisms and immersed in the passage of the for-treatment water, and a controller which controls application of potentials to the electrode and the conductive material and flow of the for-treatment water, wherein the controller performs a first treating step of applying a positive potential to the conductive material and a negative potential to the electrode with the for-treatment water flowing so as to adsorb the microorganisms on the conductive material, a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of applying an alternating voltage between the electrode and the conductive material in the presence of the for-treatment water after completion of the second treating step.

Further, a water treating apparatus of the present invention comprises an electrode to be immersed in a passage of for-treatment water, a conductive material which is capable of collecting at least microorganisms and immersed in the passage of the for-treatment water, and a controller which controls application of potentials to the electrode and the conductive material and flow of the for-treatment water, wherein the controller performs a first treating step of applying a positive potential to the conductive material and a negative potential to the electrode with the for-treatment water flowing so as to adsorb the microorganisms on the conductive material, a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and a third treating step of applying an alternating voltage between the electrode and the conductive material in the presence of the for-treatment water after completion of the second treating step.

Further, in the foregoing water treating apparatuses of the present invention, a heater for heating the for-treatment water is provided, and the controller energizes the heater in the third treating step.

Further, a water treating method of the present invention comprises a first treating step of immersing an electrode and a conductive material capable of collecting at least microorganisms in a passage of for-treatment water and applying a positive potential to the conductive material and a negative potential to the electrode so as to adsorb the microorganisms on the conductive material, a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of heating the for-treatment water by means of a heater after completion of the second treating step.

Further, a water treating method of the present invention comprises a first treating step of immersing an electrode and a conductive material capable of collecting at least microorganisms in a passage of for-treatment water and applying a positive potential to the conductive material and a negative potential to the electrode so as to adsorb the microorganisms on the conductive material, a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and a third treating step of heating the for-treatment water by means of a heater after completion of the second treating step.

Further, a water treating apparatus of the present invention comprises an electrode to be immersed in a passage of for-treatment water, a conductive material which is capable of collecting at least microorganisms and immersed in the passage of the for-treatment water, a heater for heating the for-treatment water, and a controller which controls application of potentials to the electrode and the conductive material, energization of the heater and flow of the for-treatment water, wherein the controller performs a first treating step of applying a positive potential to the conductive material and a negative potential to the electrode with the for-treatment water flowing so as to adsorb the microorganisms on the conductive material, a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of energizing the heater so as to heat the for-treatment water after completion of the second treating step.

Further, a water treating apparatus of the present invention comprises an electrode to be immersed in a passage of for-treatment water, a conductive material which is capable of collecting at least microorganisms and immersed in the passage of the for-treatment water, a heater for heating the for-treatment water, and a controller which controls application of potentials to the electrode and the conductive material, energization of the heater and flow of the for-treatment water, wherein the controller performs a first treating step of applying a positive potential to the conductive material and a negative potential to the electrode with the for-treatment water flowing so as to adsorb the microorganisms on the conductive material, a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and a third treating step of energizing the heater so as to heat the for-treatment water after completion of the second treating step.

Further, in the foregoing water treating methods or apparatuses of the present invention, application of the potentials to the electrode and conductive material is stopped in the third treating step.

Further, in the water treating apparatuses of the present invention, the electrode is disposed at a site above the conductive material where the for-treatment water flows out, the heater is disposed at a site below the conductive material where the for-treatment water flows in, and a bypassing path which causes the for-treatment water to bypass the conductive material is provided from below to above the conductive material.

Further, in the water treating apparatuses of the present invention, a pump for carrying the for-treatment water from below to above the conductive material is disposed in the bypassing path, and the controller operates the pump in the third treating step.

Further, in the water treating apparatuses of the above two present inventions, the conductive material is inclined such that the angle of the bottom of the conductive material increases toward an inlet of the bypassing path.

Further, the water treating methods or apparatuses of the present invention further comprise a treating step of discharging the for-treatment water in which the conductive material and the electrode are immersed after completion of the third treating step.

Further, in the water treating methods or apparatuses of the present invention, the conductive material is a porous material.

Further, in the water treating methods or apparatuses of the present invention, the conductive material comprises carbon fibers.

Further, in the water treating methods or apparatuses of the present invention, the carbon fibers constituting the conductive material incorporate a noble metal such as palladium, platinum, iridium or tantalum.

Further, in the water treating methods or apparatuses of the present invention, in the third treating step, chlorine and/or ozone are produced at either one of the electrode and the conductive material, and active oxygen is produced at the other.

Further, in the water treating methods or apparatuses of the present invention, the electrode incorporates a noble metal such as palladium, platinum, iridium or tantalum.

Further, a hydroponics system of the present invention is a system in which a fertilizer solution is supplied to a cultivation bed so as to cultivate plants. The system has a path which allows a secondary fertilizer solution discharged from the cultivation bed to circulate through the cultivation bed again and also has the foregoing water treating apparatus disposed in the path.

BRIEF DESCRIPTION OF THE DRAWINGS

FIG. 4 is a diagram illustrating a hydroponics system using the water treating apparatus of FIG. 1.

DETAILED DESCRIPTION OF THE PREFERRED EMBODIMENT

Figure 1:
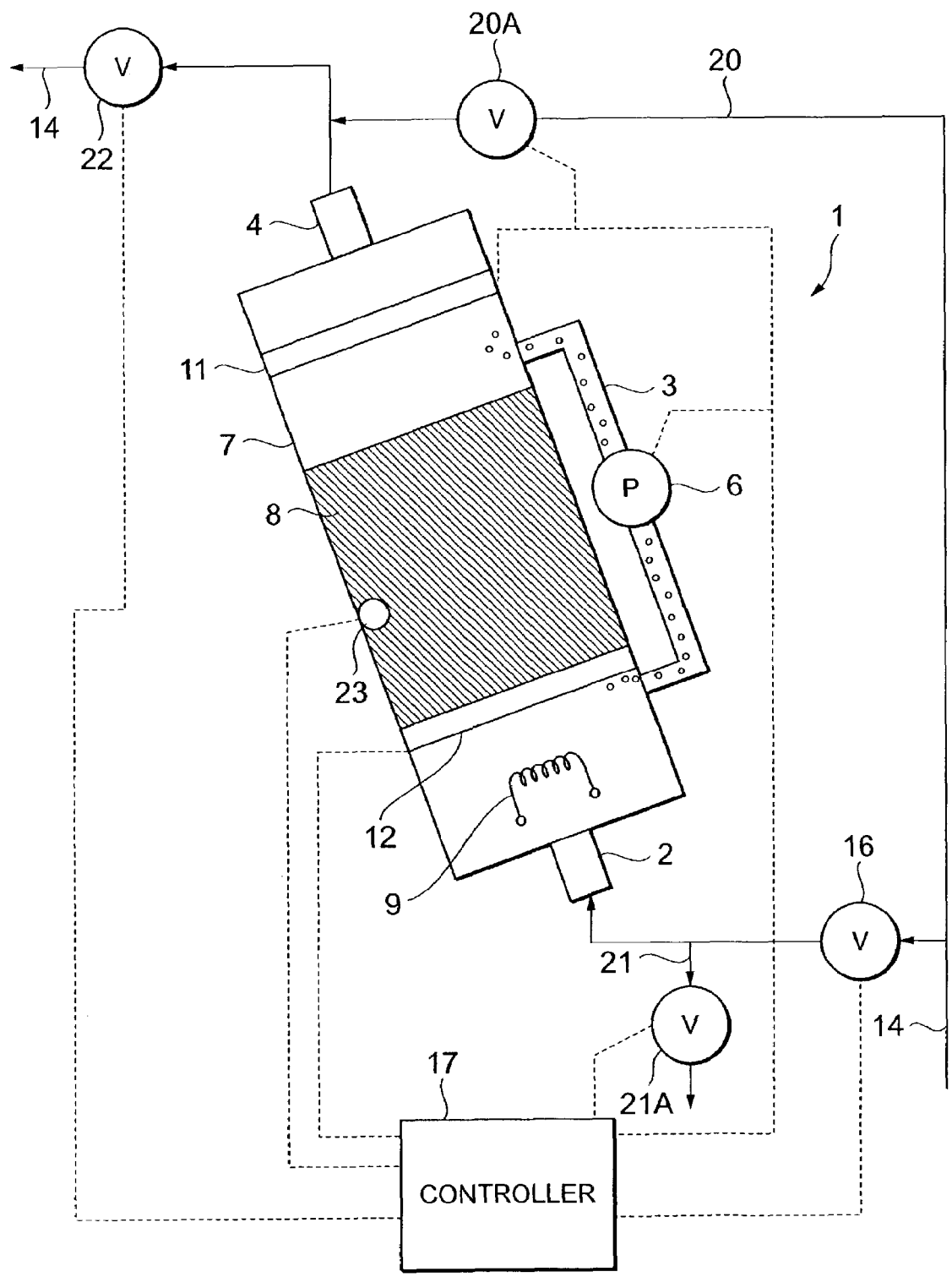
FIG. 1 is a block diagram of a water treating apparatus of an embodiment to which the present invention is applied.

Hereinafter, an embodiment of the present invention will be described in detail with reference to the drawings. FIG. 1 is a block diagram of a water treating apparatus 1 as an embodiment to which the present invention is applied. The water treating apparatus 1 comprises a case 7 which is in the shape of, for example, a cylinder and has an inlet 2 for introducing for-treatment water such as water intended for drinking and cooking which is reserved in a reservoir or waste water discharged from a hydroponics system at the lower end and an outlet 4 for discharging the for-treatment water at the upper end, water-permeable carbon fibers 8 as a conductive material which are densely stuffed in a nearly central portion in a vertical direction of the case 7, a mesh electrode 11 which is disposed at a certain distance away from the top of the carbon fibers 8 in the case 7, a mesh electrode 12 which is provided in contact with the bottom of the carbon fibers 8 so as to be in conduction, and other components.

The case 7 is disposed such that it is inclined nearly 30° from a vertical axis. Further, a bypassing path 3 is provided on the external surface of the case 7 so as to communicate the lower portion and upper portion of the case 7 to each other, bypassing the carbon fibers 8. The angle of the bottom of the carbon fibers 8 which are inclined due to the inclined case 7 increases toward an inlet of the bypassing path 3. In addition, a pump 6 is disposed in the bypassing path 3. The pump 6 is operated so as to carry for-treatment water below the carbon fibers 8 to above the carbon fibers 8.

In addition, an electric heater 9 which comprises a sheathed heater is provided in the case 7, between the bottom of the carbon fibers 8 and the inlet 2 of the case 7. When electrolyzed, the heater 9 generates heat, thereby heating for-treatment water in the case 7.

Further, the inlet 2 and the outlet 4 are connected into a feed water system 14 such as a water pipe extending from a water reservoir. In the feed water system 14, a valve 16 is disposed near and upstream from the inlet 2, and a water flow valve 22 is also connected downstream from the outlet 4. Further, a bypass pipe 20 which bypasses the water treating apparatus 1 is also connected to the water feed system 14. The bypass pipe 20 is connected between an upstream portion from the valve 16 and a portion between the outlet 4 and the water flow valve 22, and a bypass valve 20A is provided in the bypass pipe 20.

Further, between the inlet 2 and the valve 16, a drain pipe 21 having a drainage valve 21A is connected, and an end of the drain pipe 21 is communicated with a drain ditch (not shown). Reference numeral 17 denotes a controller which controls application of potentials to these electrodes 11 and 12, energization of the heater 9, operation of the pump 6, and opening and closing of the valve 16, bypass valve 20A, drainage valve 21A and water flow valve 22. Reference numeral 23 denotes a temperature sensor for sensing the temperature of the carbon fibers 8 (or for-treatment water in the case 7), and the temperature sensor 23 is connected to the controller 17.

The carbon fibers 8 are a porous conductive material and serve as a filter for for-treatment water circulating in the water treating apparatus 1. Further, the carbon fibers 8 and the electrodes 11 and 12 (the electrode 12 is in conduction with the carbon fibers 8 and faces against the electrode 11 with the carbon fibers 8 therebetween in the case 7) have a noble metal such as palladium (Pd), platinum (Pt), iridium (Ir) or tantalum (Ta) coated at least on their surfaces.

With the foregoing arrangement, operations of the controller 17 will be described hereinafter. The water treating apparatus 1 is connected into, for example, the feed water system 14 for water intended for drinking and cooking as shown in FIG. 1. Further, the controller 17 is constituted by, for instance, a general-purpose microcomputer and performs first to fourth treating steps to be described hereinafter in succession in accordance with a predetermined program.

(1) First Treating Step

Firstly, the controller 17 closes the bypass valve 20A and the drainage valve 21A and opens the valve 16 and the water flow valve 22. Thus, for-treatment water flows into the case 7 of the water treating apparatus 1 from the inlet 2, reaches the carbon fibers 8 by passing through the electrode 12, and reaches the electrode 11 by passing the inside of the carbon fibers 8. Then, the for-treatment water flows out from the outlet 4. As a result, the electrodes 11 and 12 and the carbon fibers 8 are immersed in the for-treatment water. Further, while the for-treatment water is passing through the carbon fibers 8, microorganisms such as bacteria and fungi contained in the for-treatment water are caught in fine pores formed on the surface of the carbon fibers 8 or caught and adsorbed due to affinity between the carbon fibers 8 and the microorganisms or a filtering effect of the carbon fibers 8.

Figure 2:
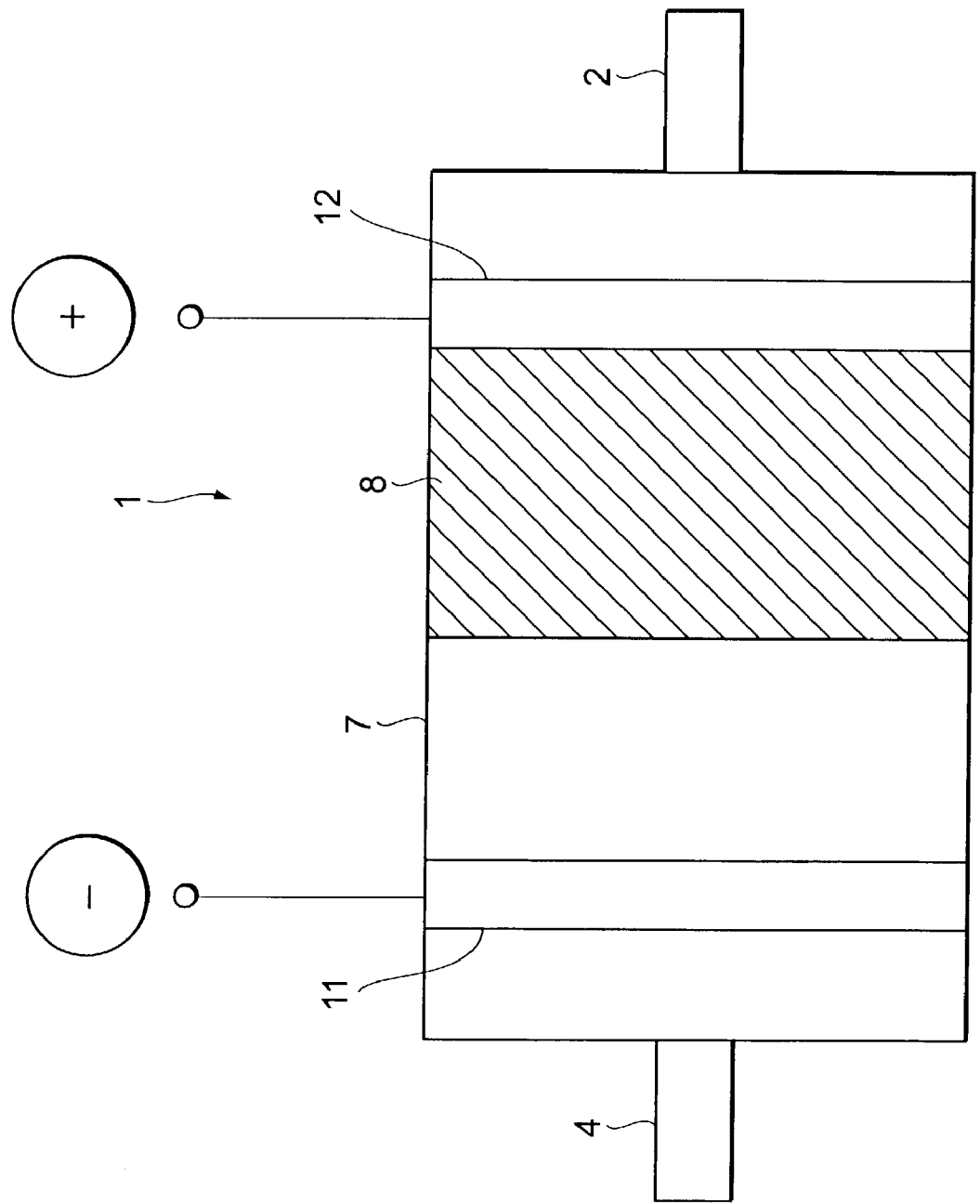
FIG. 2 is a diagram illustrating a state of the water treating apparatus of FIG. 1 when potentials are applied to carbon fibers and an electrode in first and second treating steps.

Meanwhile, the controller 17 applies a positive potential (+) to the electrode 12 which is in conduction with the carbon fibers 8 as shown in FIG. 2. Thereby, the potential of the carbon fibers 8 becomes positive. Meanwhile, a negative potential (−) is applied to the electrode 11. The potentials applied in this case are such potentials that do not cause electrolysis of water and are determined according to quality of the for-treatment water and other factors. Further, it is assumed that the case 7 shown in FIG. 2 is filled with the for-treatment water.

Then, since the potentials of the microorganisms are generally negative, the microorganisms are attracted to the carbon fibers 8 whose potential is rendered positive. Therefore, microorganisms flown into the carbon fibers 8 are attracted the surface of the carbon fibers 8 and adsorbed to fine pores in the surface smoothly and efficiently.

When the first treating step as described above is performed, for-treatment water which passes through the water treating apparatus 1 and flows out from the outlet 4 is clean water suitable for drinking and cooking from which the microorganisms have been adsorbed to the carbon fibers 8 and removed. The first treating step is performed during a period during which water intended for drinking and cooking needs to be supplied (for example, during a period during which water is supplied with a tap opened, in the case of the water channel as in the embodiment. In the case of a water reservoir as will be described later, the first treating step is performed during a predetermined period set by a timer).

Then, during a subsequent period during which the supply of the water intended for drinking and cooking is ceased (for example, in the present embodiment, a period during which the tap is being closed or a period during which the valve 16 and the water flow valve 22 are being closed by the controller 17), the controller 17 performs the second treating step.

(2) Second Treating Step

In the second treating step, the controller 17 closes the valve 16 and the water flow valve 22. Thereby, the for-treatment water remains (or is reserved) in the case 7 of the water treating apparatus 1. In this state, the controller 17 increases the potentials applied to the electrodes 11 and 12 of the carbon fibers 8, while polarities of the potentials applied to the electrodes 11 and 12 are kept, so as to cause electrolysis of the for-treatment water. The potentials applied in this case are also determined according to quality of the for-treatment water and other factors. Further, it is assumed that the case 7 in FIG. 2 is also filled with the for-treatment water.

When the potential of the carbon fibers 8 becomes positive with the for-treatment water residing in the case 7 of the water treating apparatus 1, the pH of for-treatment water in the vicinity of the surface of the carbon fibers 8 is lowered to, for example, a pH of about 2 which indicates that the for-treatment water is acidic. Hence, since the optimal pH of the microorganisms is generally around a pH of 7, the microorganisms have metabolic disorder in the for-treatment water whose pH is off the optimal pH, whereby proliferation capability and heat resistance of the microorganisms are significantly degraded. Then, since the for-treatment water surrounding the microorganisms stuck to the carbon fibers 8 becomes acidic as described above, the heat resistance of the microorganisms which can normally endure a temperature of up to about +60° C. is significantly lowered. Thus, the for-treatment water is electrolyzed during a period during which supply of water intended for drinking and cooking is ceased (for example, in the present embodiment, a period during which a tap is being closed) so as to significantly displace the pH of the for-treatment water from the optimal pH of the microorganisms. Further, since hypochlorous acid is also produced in the second treating step, sterilization with the hypochlorous acid is also conducted to a certain extent.

In the case of such microorganisms as protozoans, modification and dissolution of proteins can lead to an improvement in treatment efficiency. Therefore, in the case of for-treatment water containing a large amount of such microorganisms or positively charged microorganisms, after completion of the first treating step, another second treating step to be described hereinafter is performed in which the potential of the carbon fibers 8 (or the potential of the electrode 12) and the potential of the electrode 11 are inverted.

(3) Another Second Treating Step

Figure 3:
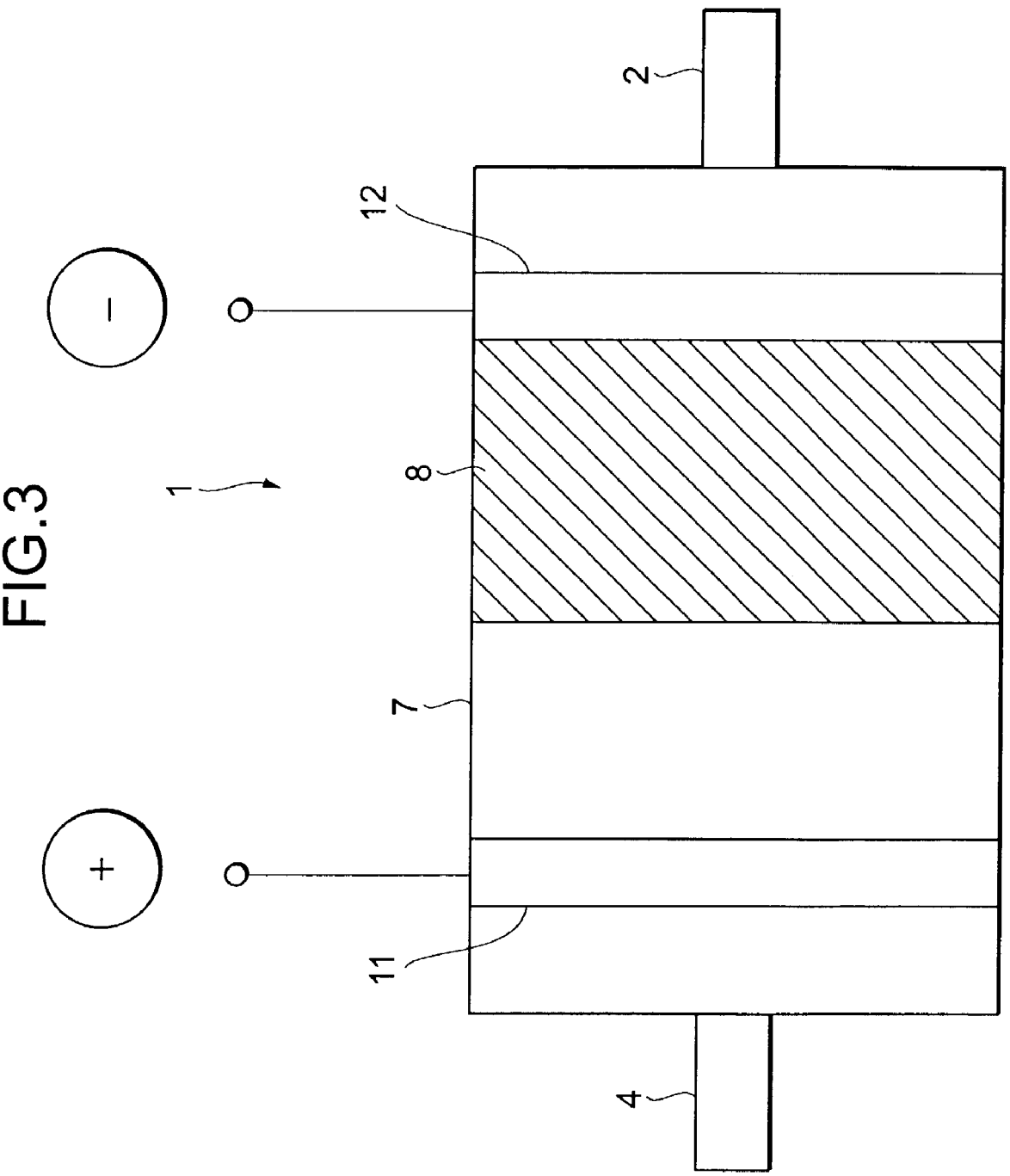
FIG. 3 is a diagram illustrating a state of the water treating apparatus of FIG. 1 when potentials are applied to the carbon fibers and the electrode in another second treating steps.

In another second treating step, the controller 17 applies a negative potential (−) to the electrode 12 which is in conduction with the carbon fibers 8 as shown in FIG. 3. Thereby, the potential of the carbon fibers 8 becomes negative. Meanwhile, a positive potential (+) is applied to the electrode 11. In this case as well, the potentials applied are determined according to quality of for-treatment water and other factors. Further, it is also assumed that the case 7 in FIG. 3 is filled with the for-treatment water.

When the potential of the carbon fibers 8 becomes negative, the pH of for-treatment water near the surface of the carbon fibers 8 is increased to, for example, a pH of about 11 which indicates that the for-treatment water is alkaline. Hence, since the for-treatment water surrounding the microorganisms stuck to the carbon fibers 8 becomes alkaline, proteins of the microorganisms such as protozoans are modified and dissolved, so that resistances thereof are lowered. Thereby, a sterilizing effect in the third treating step which is carried out subsequently to the second treating step is improved. After conducting the electrolysis of the for-treatment water in the second treating step for a predetermined time period, the controller 17 performs the third treating step.

(4) Third Treating Step

In the third treating step, the controller 17 applies an alternating voltage between the electrode 11 and the electrode 12 (carbon fibers 8). Thereby, an electric current passes through the for-treatment water and the carbon fibers 8 between the electrodes 11 and 12, so that the carbon fibers 8 and the for-treatment water generate heat. At this time, temperatures of the carbon fibers 8 and the for-treatment water are increased to at least about +50° C. (+50° C. to +100° C.). Due to the increase in temperature caused by the heat generation, even microorganisms which have stuck to the carbon fibers 8 in the first treating step and managed to survive the second treating step with reduced heat resistance can be killed efficiently in the third treating step. Since the for-treatment water has been electrolyzed in the second treating step so as to decrease or increase the pH of the for-treatment water, even microorganisms which can usually endure a temperature of up to about +60° C. can be killed at a low temperature of about +50° C.

Further, electrolysis of the for-treatment water occurs at the electrode 11 and the electrode 12 (carbon fibers 8), and at the electrode 12 (carbon fibers 8) which has a positive potential and serves as an anode electrode, chlorine ions in the for-treatment water discharge electrons so as to produce chlorine (or hypochlorous acid). In addition, oxygen atoms are bonded to decomposed water molecules so as to produce ozone. Meanwhile, at the electrode 11 which has a negative potential and serves as a cathode electrode, active oxygen is produced.

When an alternating current is applied between the electrode 12 (carbon fibers 8) and the electrode 11, the for-treatment water in the case 7 can be heated without having polarizations on the electrodes. An increase in temperature of the for-treatment water in the case 7 makes it possible to kill microorganisms whose heat resistance has been lowered by the electrolysis more efficiently.

Meanwhile, when a direct current is applied between the electrodes 12 and 11 so as to cause them to generate heat, electrolysis of the water occurs in addition to the foregoing production of ozone, energy is consumed not only for the heat generation but also for the electrolysis. In contrast, the application of the alternating current does not cause electrolysis of the water and can kill the microorganisms with a small consumption of electric power. As a result, a significant degree of energy conservation can be achieved, which is considered economically advantageous. Further, since the alternating current does not involve a chemical reaction, it is also expected that useful lives of the electrodes can be prolonged.

At this time, since the electrodes 11 and 12 and the carbon fibers 8 have a noble metal such as palladium, platinum, iridium or tantalum incorporated therein, chlorine and/or ozone are vigorously produced at the anode, and active oxygen is vigorously produced at the cathode. These chlorine (hypochlorous acid), ozone and active oxygen can also kill microorganisms caught on the surface of the carbon fibers 8 and present in the for-treatment water.

(5) Another Third Treating Step

In place of application of an alternating voltage to the electrodes 11 and 12 (in the third treating step of the above (4)), the for-treatment water and the carbon fibers 8 may be heated by means of an electric heater 9. In this case, the controller 17 energizes (or applies an alternating voltage to) the electric heater 9 so as to cause the heater 9 to generate heat which in turn heats the carbon fibers 8 and the for-treatment water.

In this case as well, temperatures of the carbon fibers 8 and the for-treatment water are increased to at least about +50° C. (+50° C. to +100° C.). Due to the increase in temperature caused by the heat generation, even microorganisms which have stuck to the carbon fibers 8 in the first treating step and managed to survive the second treating step with reduced heat resistance can be killed efficiently in this alternative third treating step. Since the for-treatment water has been electrolyzed in the foregoing second treating step so as to decrease or increase the pH of the for-treatment water, even microorganisms which can usually endure a temperature of up to about +60° C. can be killed at a low temperature of about +50° C.

At this time, due to the heat generation of the electric heater 9, bubbles are produced in a space below the carbon fibers 8 (electrode 12) in the case 7. Since these bubbles cannot pass through the carbon fibers 8 easily, presence of the bubbles remaining in the space below the carbon fibers 8 (electrode 12) in the case 7 eventually hinders treatment of the for-treatment water. For this reason, while energizing the electric heater 9, the controller 17 operates the pump 6 so as to carry the bubbles below the carbon fibers 8 together with a small amount of for-treatment water to above the carbon fibers 8 (as shown in FIG. 1). The carried bubbles are then discharged from the outlet 4.

Thereby, the inconvenience that the bubbles produced by the heat generation of the electric heater 9 are accumulated in the case 7 can be obviated. The controller 17 controls energization of the electric heater 9 based on an output from the temperature sensor 23. Further, the pump 6 can be operated continuously or intermittently during the energization of the electric heater 9. Alternatively, independently of the energization of the electric heater 9, the pump 6 may be operated continuously or intermittently in this alternative third treating step. Further, the pump 6 may be controlled based on an increase in temperature of the for-treatment water (carbon fibers 8) which is detected by the temperature sensor 23.

Further, in this alternative third treating step, in addition to the heat generation of the electric heater 9, an alternating voltage may be applied between the electrode 11 and the electrode 12 (carbon fibers 8) so as to cause the for-treatment water and the carbon fibers 8 to generate heat, as in the third treating step of the above (4). According to the constitution, the temperature of the for-treatment water (carbon fibers 8) in the third treating step can be increased rapidly, and the effect of treating the microorganisms can be improved.

Then, after killing the microorganisms in the third treating step, the controller 17 performs the fourth treating step.

(5) Fourth Treating Step

In the fourth treating step, the controller 17 opens the bypass valve 20A and the drainage valve 21A with the valve 16 and the water flow valve 22 being closed, after completion of the third treating step. Thereby, for-treatment water from the feed water system 14 flows into the case 7 from the outlet 4, flows through the inside of the case 7, flows out from the inlet 2, and is discharged to the drain ditch through the drain pipe 21.

In this case, a negative potential is applied to the electrode 12 so as to make the potential of the carbon fibers 8 negative and cause the resulting carbon fibers 8 to repel microorganisms having a negative potential. As a result, the microorganisms are removed from the carbon fibers 8 or become more easily removable. Thereby, microorganisms entered through the inlet 2 and stuck to the carbon fibers 8 are removed from the carbon fibers 8 easily by for-treatment water flowing into the case 7 through the outlet 4 and passing through the carbon fibers 8 toward the inlet 2 and then discharged to the drain ditch through the drain pipe 21. Thus, the carbon fibers 8 can be restored to its initial clean state free from microorganisms, and the carbon fibers 8 and the electrodes 11 and 12 can be kept clean.

As described above, in the second treating step and the third treating step, microorganisms stuck to the carbon fibers 8 are killed, and in the fourth treating step, for-treatment water is flown into the treating apparatus 1 from the outlet 4 and discharged through the drain pipe 21 which is connected between the inlet 2 and the valve 16. Thereby, microorganisms which are already killed but still stuck to the carbon fibers 8 can be removed and washed out from the carbon fibers 8 and discharged to the drain ditch. As a result, a good microorganisms adsorbing effect of the carbon fibers 8 can be reproduced next time the first treating step is performed.

(6) Hydroponics System

Next, an embodiment of a hydroponics system 30 which has the water treating apparatus 1 of the present invention incorporated therein will be described with reference to FIG. 4. In FIG. 4, a secondary fertilizer solution (which is a fertilizer solution nutrients of which have been absorbed and decreased by plants in a cultivation bed 35) which is reserved in a fertilizer solution reservoir 36 is sent to a filtration tank 31 which contains activated carbon by a circulation pump 37 so as to remove impurities such as organic matter from the solution. Thereafter, the resulting solution flows into a solution reservoir 32 to be reserved temporarily. The fertilizer solution (for-treatment water) reserved in the solution reservoir 32 then flows into a cartridge filter 33 which comprises a bobbin filter or the like so as to remove impurities which have not been removed in the filtration tank 31. Then, the resulting solution flows into the water treating tank 1 from the inlet 2.

After flowing into the water treating apparatus 1, the fertilizer solution is electrolyzed therein. Thereby, bacteria proliferating in the fertilizer solution, particularly Fusariums or other bacteria (thereafter referred to as "pathogenic bacteria") which damage roots of crops 38 as plants in the cultivation bed 35 are adsorbed to the carbon fibers 8, and only the fertilizer solution from which the pathogenic bacteria have been removed flows into a fertilizer solution preparation tank 34 from the outlet 4 of the water treating apparatus 1. For example, when the second treating step (electrolysis) is carried out once in a day with the valve 16 and the water flow valve 22 closed, the fertilizer solution becomes an acidic solution having a pH of about 2. Thereby, the pathogenic bacteria adsorbed to the carbon fibers 8 undergo metabolic disorder since the pH of the fertilizer solution is off the optimal pH of the pathogenic bacteria, so that proliferation capability and heat resistance of the pathogenic bacteria are significantly degraded.

After the proliferation capability and heat resistance of the pathogenic bacteria are significantly degraded due to the electrolysis of the fertilizer solution, the third treating step in which an alternating voltage is applied between the electrode 11 and the electrode 12 (carbon fibers 8) is carried out. When the alternating voltage is applied, the fertilizer solution in the case 7 generates heat by which the pathogenic bacteria are heated. Thereby, the pathogenic bacteria which have undergone the metabolic disorder are killed.

Then, after completion of the third treating step, the bypass valve 20A and the drainage valve 21A in the water treating apparatus 1 are opened so as to discharge the pathogenic bacteria adsorbed to the carbon fibers 8 and killed to the drain ditch through the drain pipe 21, and the carbon fibers are washed to be clean. Reference numeral 40 denotes service water (in this case, tap water or underground water is used as the service water). Since the fertilizer solution circulating though a circulation path is decreased due to absorption into the crops 38 or natural evaporation, a decreased amount of the fertilizer solution is replenished with the service water 40.

Further, when the fertilizer solution in the cultivation bed 35 lacks certain kinds of nutrients which are required for growth of the crops 38 planted in the cultivation bed 35, the insufficient nutrients are selected from fertilizer adjusting devices 34A, 34B, 34C and 34D (in this case, magnesium (Mg), iron (Fe), manganese (Mn), copper (Cu) or other fertilizers (nutrients) which are assumed to be apt be insufficient for growing the crops 38 are independently reserved in the fertilizer adjusting devices 34A, 34B, 34C and 34D) and charged into the fertilizer solution preparation tank 34.

Thereby, the fertilizer solution in the fertilizer solution preparation tank 34 is adjusted to be a fertilizer solution containing nutrients suitable for growing the crops 38 planted in the cultivation bed 35. Then, the fertilizer solution having its nutrients adjusted to be suitable for growing the crops 38 flows from the fertilizer solution preparation tank 34 into the cultivation bed 35 in which the corps 38 are planted, and a predetermined amount of the fertilizer solution is adsorbed by the crops 38. Then, the secondary fertilizer solution having a reduced amount of the nutrients is discharged from the cultivation bed 35, returns to the fertilizer solution reservoir 36, is sent out by the circulation pump 37 again, and re-circulates as a recycled solution.

Thus, since the water treating apparatus 1 of the present invention is disposed in the path to re-circulate a secondary fertilizer solution discharged from the cultivation bed 35 through the cultivation bed 35, the optimal pH of pathogenic bacteria contained in a fertilizer solution which circulates through the path in which a fertilizer solution and a secondary fertilizer solution flow can be significantly displaced, and the pathogenic bacteria can be heated. Thereby, pathogenic bacteria existing in a circulation path in the cultivation bed 35 undergo metabolic disorder, and the pathogenic bacteria which have undergone the metabolic disorder can be killed by heating. Thus, as compared with conventional heat sterilization of a fertilizer solution by use of a heater, inconvenience of consuming a large amount of energy can be avoided, and a significant degree of energy conservation can be achieved.

Further, since sterilization of the pathogenic bacteria proliferating in the fertilizer solution is not carried out by use of ozone or ultraviolet radiation, decreases in concentrations of iron and manganese contained in the fertilizer solution can be inhibited. Thereby, iron and manganese deficiencies of the crops 38 being cultivated in the cultivation bed 35 can be prevented. In addition, deleterious effects of toxic substances remaining or accumulating in crops 38 on the crops 38 or humans and livestock that have eaten the crops 38 can be inhibited. On the whole, the effect of eliminating pathogenic bacteria in the circulation path can be significantly improved, and it becomes possible to cultivate clean and sanitary crops 38.

In the embodiments, a positive potential (+) is applied to the electrode 12 of the carbon fibers 8 and a negative potential (−) is applied to the electrode 11 in one of the two second treating steps, and a negative potential (−) is applied to the electrode 12 of the carbon fibers 8 and a positive potential (+) is applied to the electrode 11 in the other second treating step. Alternatively, after the first treating step, the two types of the second treating steps may be performed alternately. In other words, the present invention is still effective in such a constitution that a positive potential (+) and a negative potential (−) are alternately applied to the electrode 12 of the carbon fibers 8 and the electrode 11 in the treating step (i.e., second treating step) subsequent to the first treating step so as to kill microorganisms whose optimal pH is acidic or alkaline.

Further, in the first embodiment, the water treating apparatus 1 is disposed in the water channel such as a water pipe from the solution reservoir. Alternatively, the apparatus 1 may be directly disposed in the solution reservoir. It is also effective to dispose the apparatus 1 in the waste channel. In addition, although the carbon fibers are used as the conductive material in the embodiment, it may be any conductive material as long as it is capable of collecting microorganisms.

Further, in the embodiment, microorganisms adsorbed to the carbon fibers 8 and killed are discharged from the inlet 2 to the drain pipe 21 connected between the inlet 2 and the valve 16 by injecting for-treatment water into the water treating apparatus 1 from the outlet 4. Alternatively, the carbon fibers 8 (having meshes so as to secure water permeability) may be washed by injecting for-treatment water into the inlet 2 and discharging the for-treatment water from the outlet 4. In that case as well, a negative potential is applied to the electrode 12 so as to make the potential of the carbon fibers 8 negative and cause the carbon fibers 8 to repel microorganisms having a negative potential, and after the microorganisms are thereby removed or become more easily removable from the carbon fibers 8, for-treatment water is injected into the inlet 2.

Further, in the latter embodiment, the water treating apparatus 1 of the present invention is disposed between the cartridge filter 33 and fertilizer solution preparation tank 34 of the hydroponics system 30. Alternatively, the water treating apparatus 1 may be disposed anywhere in a circulation path through which a fertilizer solution and a secondary fertilizer solution circulate. In addition, although the water treating apparatus 1 is disposed at only one location in the hydroponics system 30 in the embodiment, the present invention is also effective even when the water treating apparatus 1 is disposed at two or more locations in the circulation path through which the fertilizer solution and the secondary fertilizer solution circulate.

Further, although the water treating apparatus of the present invention is applied to the hydroponics system in the embodiment, it may also be applied to a fish hatchery for sea fish or freshwater fish so as to kill saprophytic bacteria or microorganisms in sea water or fresh water.

As described in detail above, according to the present invention, firstly, microorganisms contained in for-treatment water are collected on a conductive material in the first treating step. At this time, since the potential of the microorganisms is negative, the microorganisms are attracted to the conductive material having a positive potential. Thereby, the microorganisms are stuck to the conductive material smoothly and efficiently.

Then, in the second treating step, flow of the for-treatment water is stopped, and potentials applied to the conductive material and the electrode are increased while polarities of the potentials applied to the conductive material and the electrode are kept, so as to carry out electrolysis of the for-treatment water. Thereby, the pH of for-treatment water near the surface of the conductive material decreases, the for-treatment water becomes acidic, and the pH of the for-treatment water surrounding the microorganisms can be significantly displaced from the optimal pH of the microorganisms. Further, hypochlorous acid is also produced on the surface of the conductive material at the same time. Since the microorganisms metabolize with enzyme, the microorganisms undergo metabolic disorder in the for-treatment water whose pH is off the optimal pH of the microorganisms, whereby proliferation capability and heat resistance of the microorganisms are significantly degraded. Thereby, it becomes possible to kill the microorganisms with a smaller increase in temperature. In addition, sterilization by hypochlorous acid occurs to a certain extent in the second treating step.

Then, in the third treating step, an alternating voltage is applied between the electrode and the conductive material, whereby the for-treatment water generates heat. Due to an increase in temperature caused by the heat generation, the microorganisms stuck to the conductive material and suffering from the metabolic disorder due to the pH of the for-treatment water which is off the optimal pH of the microorganisms are killed. With the forgoing effects, according to the present invention, when the pH of for-treatment water such as water intended for drinking and cooking or waste water can be significantly displaced from the optimal pH of microorganisms, the microorganisms can be stuck to a conductive material and killed efficiently with a small increase in temperature, and an effect of removing microorganisms in for-treatment water can be improved significantly.

Further, according to the present invention, firstly, microorganisms contained in for-treatment water are collected on a conductive material in the first treating step. At this time, since the potential of the microorganisms is negative, the microorganisms are attracted to the conductive material having a positive potential. Thereby, the microorganisms are stuck to the conductive material smoothly and efficiently.

Then, in the second treating step, flow of the for-treatment water is stopped, and polarities of the potentials applied to the conductive material and the electrode are inverted, and potentials applied to the conductive material and the electrode are increased so as to carry out electrolysis of the for-treatment water. Thereby, the pH of for-treatment water near the surface of the conductive material increases, the for-treatment water becomes alkaline, and the pH of the for-treatment water surrounding the microorganisms can be significantly displaced from the optimal pH of the microorganisms. Since the microorganisms metabolize with enzyme, the microorganisms undergo metabolic disorder in the for-treatment water whose pH is off the optimal pH of the microorganisms, whereby proliferation capability and heat resistance of the microorganisms are significantly degraded. Thereby, it becomes possible to kill the microorganisms with a smaller increase in temperature.

Then, in the third treating step, an alternating voltage is applied between the electrode and the conductive material, whereby the for-treatment water generates heat. Due to an increase in temperature caused by the heat generation, the microorganisms stuck to the conductive material and suffering from the metabolic disorder due to the pH of the for-treatment water which is off the optimal pH of the microorganisms are killed. With the forgoing effects, according to the present invention, microorganisms contained in for-treatment water such as water intended for drinking and cooking or waste water can be stuck to a conductive material and killed efficiently, and an effect of removing microorganisms in for-treatment water can be improved significantly.

Further, according to the present invention, in the foregoing third treating step, the foregoing for-treatment water is heated by means of a heater. Therefore, in addition to the application of the alternating voltage between the electrode and the conductive material, the for-treatment water is also heated by means of the heater, so that the temperature of the for-treatment water increases more quickly. Thereby, it becomes possible to kill the microorganisms stuck to the conductive material more quickly and more efficiently.

Further, according to the present invention, firstly, microorganisms contained in for-treatment water are collected on a conductive material in the first treating step. At this time, since the potential of the microorganisms is negative, the microorganisms are attracted to the conductive material having a positive potential. Thereby, the microorganisms are stuck to the conductive material smoothly and efficiently.

Then, in the second treating step, flow of the for-treatment water is stopped, and potentials applied to the conductive material and the electrode are increased while polarities of the potentials applied to the conductive material and the electrode are kept, so as to carry out electrolysis of the for-treatment water. Thereby, the pH of for-treatment water near the surface of the conductive material decreases, the for-treatment water becomes acidic, and the pH of the for-treatment water surrounding the microorganisms can be significantly displaced from the optimal pH of the microorganisms. Further, hypochlorous acid is also produced on the surface of the conductive material at the same time. Since the microorganisms metabolize with enzyme, the microorganisms undergo metabolic disorder in the for-treatment water whose pH is off the optimal pH of the microorganisms, whereby proliferation capability and heat resistance of the microorganisms are significantly degraded. Thereby, it becomes possible to kill the microorganisms with a smaller increase in temperature. In addition, sterilization by hypochlorous acid occurs to a certain extent in the second treating step.

Then, in the third treating step, the for-treatment water is heated by means of a heater. Due to an increase in temperature of the for-treatment water caused by the heating, the microorganisms stuck to the conductive material and suffering from the metabolic disorder due to the pH of the for-treatment water which is off the optimal pH of the microorganisms are killed. With the forgoing effects, according to the present invention, when the pH of for-treatment water such as water intended for drinking and cooking or waste water can be significantly displaced from the optimal pH of microorganisms, the microorganisms can be stuck to a conductive material and killed efficiently with a small increase in temperature, and an effect of removing microorganisms in for-treatment water can be improved significantly.

Further, according to the present invention, firstly, microorganisms contained in for-treatment water are collected on a conductive material in the first treating step. At this time, since the potential of the microorganisms is negative, the microorganisms are attracted to the conductive material having a positive potential. Thereby, the microorganisms are stuck to the conductive material smoothly and efficiently.

Then, in the second treating step, flow of the for-treatment water is stopped, and polarities of the potentials applied to the conductive material and the electrode are inverted and potentials applied to the conductive material and the electrode are increased so as to carry out electrolysis of the for-treatment water. Thereby, the pH of for-treatment water near the surface of the conductive material increases, the for-treatment water becomes alkaline, and the pH of the for-treatment water surrounding the microorganisms can be significantly displaced from the optimal pH of the microorganisms. Since the microorganisms metabolize with enzyme, the microorganisms undergo metabolic disorder in the for-treatment water whose pH is off the optimal pH of the microorganisms, whereby proliferation capability and heat resistance of the microorganisms are significantly degraded. Thereby, it becomes possible to kill the microorganisms with a smaller increase in temperature.

Then, in the third treating step, the for-treatment water is heated by means of a heater. Due to an increase in temperature of the for-treatment water by the heating, the microorganisms stuck to the conductive material and suffering from the metabolic disorder due to the pH of the for-treatment water which is off the optimal pH of the microorganisms are killed. With the forgoing effects, according to the present invention, microorganisms contained in for-treatment water such as water intended for drinking and cooking or waste water can be stuck to a conductive material and killed efficiently, and an effect of removing microorganisms in for-treatment water can be improved significantly.

Further, according to the present invention, in the foregoing third treating step, the application of the potentials to the electrode and the conductive material is stopped. Therefore, power consumption which is increased by energization of the heater can be minimized.

Further, according to the present invention, the foregoing electrode is disposed near a for-treatment water outlet provided above the conductive material, and the foregoing heater is provided near a for-treatment water inlet provided below the conductive material. Thereby, the for-treatment water is heated by the heater smoothly. In addition, a bypassing path for the for-treatment water is provided which bypasses the conductive material from below to above the conductive material. Thereby, bubbles generated below the conductive material by heat generated by the heater can be moved to above the conductive material through the bypassing path so as to be discharged, and the inconvenience that the bubbles are accumulated below the conductive material and inhibit the treatments of the for-treatment water can be avoided.

Further, according to the present invention, a pump for carrying the for-treatment water from below to above the conductive material is provided in the bypassing path, and the controller operates the pump in the third treating step. Thereby, bubbles generated below the conductive material when the heater generates heat can be smoothly carried to above the conductive material and discharged.

Further, according to the present invention, the conductive material is inclined such that the angle of the bottom of the conductive material increases toward an inlet of the bypassing path. Thereby, bubbles generated below the conductive material can enter the bypassing path easily, and the bubbles can be dealt with more smoothly.

Further, according to the present invention, after completion of the third treating step, the microorganisms collected on the conductive material and killed can be washed out. In this case, since the for-treatment water in which the conductive material and the electrode are immersed is discharged, microorganisms stuck to the conductive material and the electrode can be removed easily by running water. Thereby, the conductive material and the electrode can be kept clean.

Further, according to the present invention, the conductive material is a porous material. Thereby, an effect of collecting microorganisms can be improved significantly. According to the invention of claim 17, the conductive material comprises carbon fibers. As a result, the effect of collecting the microorganisms in the first treating step and the effect of displacing the pH of the for-treatment water from the optimal pH of the microorganisms by electrolysis in the second treating step can be improved.

Further, according to the present invention, the carbon fibers constituting the conductive material have a noble metal such as palladium, platinum, iridium or tantalum incorporated therein. Thereby, deterioration of the conductive material comprising the carbon fibers is inhibited so as to achieve a long useful life of the conductive material, and hypochlorous acid can be produced efficiently.

Further, according to the present invention, in the foregoing third treating step, chlorine and/or ozone are/is produced at one of the electrode and the conductive material, and active oxygen is produced at the other. Thereby, in the third treating step, microorganisms can also be killed by chlorine and/or ozone produced by electrolysis at one of the electrode and conductive material having a positive potential and active oxygen produced by the electrolysis at the other having a negative potential.

Further, according to the present invention, the electrodes have a noble metal such as palladium, platinum, iridium or tantalum incorporated therein. Thereby, the efficiency of production of chlorine and/or ozone and active oxygen at the electrodes can be further improved.

Further, according to the present invention, a fertilizer solution is supplied to a cultivation bed so as to cultivate plants, a path for recirculating a secondary fertilizer solution discharged from the cultivation bed through the cultivation bed, and the foregoing water treating apparatus is disposed in the path. Consequently, pathogenic bacteria existing in the circulation path in the cultivation bed can be killed securely by significantly displacing the optimal pH of the pathogenic bacteria to cause them to undergo metabolic disorder and then heating the pathogenic bacteria. Thereby, as compared with conventional heat sterilization of a fertilizer solution, for example, a large amount of energy is not required. Therefore, the pathogenic bacteria in the cultivation bed can be significantly decreased with a small amount of energy, and a significant degree of energy conservation can be achieved accordingly.

Further, since sterilization of the pathogenic bacteria proliferating in the fertilizer solution is not carried out by use of a bactericide and ultraviolet radiation as in the case of, for example, the prior art, decreases in concentrations of iron and manganese contained in the fertilizer solution can be inhibited, and the effect of removing the pathogenic bacteria in the circulation path can be significantly improved. Thereby, iron and manganese deficiencies of plants cultivated in the cultivation bed can be prevented. In addition, deleterious effects of toxic substances which may remain or accumulate in plants when a bactericide is used on the plants and humans and livestock that have eaten the plants can be inhibited. As a result, it becomes possible to cultivate clean and sanitary plants.

What is claimed is:

1. A water treating method comprising:
   a first treating step of immersing an electrode and a conductive material capable of collecting at least microorganisms in a passage of for-treatment water and applying a positive potential to the conductive material and a negative potential to the electrode so as to adsorb the microorganisms on the conductive material,
   a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and
   a third treating step of applying an alternating voltage between the electrode and the conductive material in the presence of the for-treatment water after completion of the second treating step.

2. A water treating method comprising: a first treating step of immersing an electrode and a conductive material capable of collecting at least microorganisms in a passage of for-treatment water and applying a positive potential to the conductive material and a negative potential to the electrode so as to adsorb the microorganisms on the conductive material,
   a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and
   a third treating step of applying an alternating voltage between the electrode and the conductive material in the presence of the for-treatment water after completion of the second treating step.

3. The method of claim 1 or 2, wherein the for-treatment water is heated by means of a heater in the third treating step.

4. A water treating method comprising:
   a first treating step of immersing an electrode and a conductive material capable of collecting at least microorganisms in a passage of for-treatment water and applying a positive potential to the conductive material and a negative potential to the electrode so as to adsorb the microorganisms on the conductive material,
   a second treating step of stopping flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and
   a third treating step of heating the for-treatment water by means of a heater after completion of the second treating step.

5. A water treating method comprising:
   a first treating step of immersing an electrode and a conductive material capable of collecting at least microorganisms in a passage of for-treatment water and applying a positive potential to the conductive material and a negative potential to the electrode so as to adsorb the microorganisms on the conductive material,
   a second treating step of stopping flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and
   a third treating step of heating the for-treatment water by means of a heater after completion of the second treating step.

6. The method of claim 4 or 5, wherein application of the potentials to the electrode and the conductive material is stopped in the third treating step.

7. The method of claim 1, 2, 4 or 5, further comprising a treating step of discharging the for-treatment water in which the conductive material and the electrode are immersed after completion of the third treating step.

8. The method of claim 1, 2, 4 or 5, wherein in the third treating step, chlorine and/or ozone are produced at either one of the electrode and the conductive material, and active oxygen is produced at the other.

9. A water treating apparatus comprising:
   an electrode to be immersed in a passage of for-treatment water,
   a conductive material which is a porous material or carbon fibers, and is immersed in the passage of the for-treatment water, and
   a controller which controls application of potentials to the electrode and the conductive material and flow of the for-treatment water,
   wherein the controller performs a first treating step of applying a positive potential to the conductive material and a negative potential to the electrode with the for-treatment water flowing so as to adsorb the microorganisms on the conductive material, a second treating step of stopping the flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of applying an alternating voltage between the electrode and the conductive material in the presence of the for-treatment water after completion of the second treating step.

10. A water treating apparatus comprising:
an electrode to be immersed in a passage of for-treatment water,
a conductive material which is a porous material or carbon fibers, and is immersed in the passage of the for-treatment water, and
a controller which controls application of potentials to the electrode and the conductive material and flow of the for-treatment water,
wherein the controller performs a first treating step of applying a positive potential to the conductive material and a negative potential to the electrode with the for-treatment water flowing so as to adsorb the microorganisms on the conductive material, a second treating step of stopping the flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for-treatment water, and a third treating step of applying an alternating voltage between the electrode and the conductive material in the presence of the for-treatment water after completion of the second treating step.

11. The apparatus of claim 9 or 10, wherein a heater for heating the for-treatment water is provided, and the controller energizes the heater in the third treating step.

12. The apparatus of claim 11, wherein the electrode is disposed at a site above the conductive material where the for-treatment water flows out, the heater is disposed at a site below the conductive material where the for-treatment water flows in, and a bypassing path which causes the for-treatment water to bypass the conductive material is provided from below to above the conductive material.

13. The apparatus of claim 12, wherein a pump for carrying the for-treatment water from below to above the conductive material is disposed in the bypassing path, and the controller operates the pump in the third treating step.

14. The apparatus of claim 12, wherein the conductive material is inclined such that the angle of the bottom of the conductive material increases toward an inlet of the bypassing path.

15. A water treating apparatus comprising:
an electrode to be immersed in a passage of for-treatment water,
a conductive material which is a porous material or carbon fibers, and is immersed in the passage of the for-treatment water,
a heater for heating the for-treatment water, and
a controller which controls application of potentials to the electrode and the conductive material, energization of the heater and flow of the for-treatment water,
wherein the controller performs a first treating step of applying a positive potential to the conductive material and a negative potential to the electrode with the for-treatment water flowing so as to adsorb the microorganisms on the conductive material, a second treating step of stopping the flow of the for-treatment water after completion of the first treating step and increasing the potentials applied to the conductive material and the electrode in the presence of the for-treatment water, while polarities of the potentials applied to the conductive material and the electrode are kept, so as to cause electrolysis of the for-treatment water, and a third treating step of energizing the heater so as to heat the for-treatment water after completion of the second treating step.

16. The apparatus of claim 15, wherein the electrode is disposed at a site above the conductive material where the for-treatment water flows out, the heater is disposed at a site below the conductive material where the for-treatment water flows in, and a bypassing path which causes the for-treatment water to bypass the conductive material is provided from below to above the conductive material.

17. A water treating apparatus comprising:
an electrode to be immersed in a passage of for-treatment water,
a conductive material which is a porous material or carbon fibers, and is immersed in the passage of the for-treatment water,
a heater for heating the for-treatment water, and
a controller which controls application of potentials to the electrode and the conductive material, energization of the heater and flow of the for-treatment water,
wherein the controller performs a first treating step of applying a positive potential to the conductive material and a negative potential to the electrode with the for-treatment water flowing so as to adsorb the microorganisms on the conductive material, a second treating step of stopping the flow of the for-treatment water after completion of the first treating step, inverting polarities of the potentials applied to the conductive material and the electrode in the presence of the for-treatment water, and increasing the potentials applied to the conductive material and the electrode so as to cause electrolysis of the for- treatment water, and a third treating step of energizing the heater so as to heat the for-treatment water after completion of the second treating step.

18. The apparatus of claim 17, wherein the electrode is disposed at a site above the conductive material where the for-treatment water flows out, the heater is disposed at a site below the conductive material where the for-treatment water flows in, and a bypassing path which causes the for-treatment water to bypass the conductive material is provided from below to above the conductive material.

19. The apparatus of claim 9, 10, 15 or 17, wherein the conductive material is a porous material.

20. The apparatus of claim 9, 10, 15 or 17, wherein the conductive material comprises carbon fibers.

21. The apparatus of claim 20, wherein the carbon fibers constituting the conductive material incorporate a noble metal such as palladium, platinum, iridium or tantalum.

22. The apparatus of claim 9, 10, 15 or 17, wherein the electrode incorporates a noble metal such as palladium, platinum, iridium or tantalum.

* * * * *